United States Patent
Schechner et al.

(10) Patent No.: US 8,865,033 B2
(45) Date of Patent: Oct. 21, 2014

(54) PROCESS FOR PRODUCING A DENTAL APPLIANCE

(75) Inventors: Gallus Schechner, Seefeld (DE); Michael Jahns, Gilching (DE); Martin Goetzinger, Eching am Ammersee (DE)

(73) Assignee: 3M Innovative Properties Company, St. Paul, MN (US)

( * ) Notice: Subject to any disclaimer, the term of this patent is extended or adjusted under 35 U.S.C. 154(b) by 634 days.

(21) Appl. No.: 13/060,127

(22) PCT Filed: Oct. 1, 2009

(86) PCT No.: PCT/US2009/059154
§ 371 (c)(1),
(2), (4) Date: Feb. 22, 2011

(87) PCT Pub. No.: WO2010/039910
PCT Pub. Date: Apr. 8, 2010

(65) Prior Publication Data
US 2011/0151411 A1    Jun. 23, 2011

(30) Foreign Application Priority Data
Oct. 1, 2008 (EP) .................... 08165607

(51) Int. Cl.
| | | |
|---|---|---|
| *A61C 13/00* | (2006.01) | |
| *A61K 6/06* | (2006.01) | |
| *C03B 19/12* | (2006.01) | |
| *C04B 35/14* | (2006.01) | |
| *C04B 35/624* | (2006.01) | |
| *C03C 4/00* | (2006.01) | |
| *C03C 12/00* | (2006.01) | |
| *A61K 6/00* | (2006.01) | |
| *A61K 6/02* | (2006.01) | |
| *A61K 6/027* | (2006.01) | |

(52) U.S. Cl.
CPC ......... *A61C 13/0022* (2013.01); *A61C 13/0006* (2013.01); *A61K 6/0662* (2013.01); *C04B 35/624* (2013.01); *C04B 35/14* (2013.01); *C03B 19/12* (2013.01); *C03C 4/0021* (2013.01); *C03C 12/00* (2013.01); *A61K 6/0008* (2013.01); *A61K 6/024* (2013.01); *A61K 6/025* (2013.01); *A61K 6/0255* (2013.01); *A61K 6/0273* (2013.01)
USPC .......... 264/16; 264/621; 433/222.1; 433/223

(58) Field of Classification Search
None
See application file for complete search history.

(56) References Cited

U.S. PATENT DOCUMENTS

| | | |
|---|---|---|
| 3,810,773 A | 5/1974 | Shannon |
| 4,078,310 A | 3/1978 | Horger |

(Continued)

FOREIGN PATENT DOCUMENTS

| | | |
|---|---|---|
| CN | 1257851 | 6/2000 |
| CN | 1594196 | 3/2005 |

(Continued)

OTHER PUBLICATIONS

Buckley et al., J. Chem. Ed. Jul. 1994, vol. 71, Issue 7, pp. 599-602.*

(Continued)

*Primary Examiner* — Benjamin Schiffman
(74) *Attorney, Agent, or Firm* — Nicole J. Einerson (57) ABSTRACT

The invention relates to a process for producing a dental appliance, the process comprising the steps of a) providing a mixture of a liquid, an inorganic binder precursor being able to undergo a sol/gel reaction and a glass or glass ceramic powder, b) casting the mixture into a mold, c) drying the cast mixture in the mold to obtain a machinable dental appliance, d) optionally machining the dental appliance to obtain a dental workpiece, e) optionally removing the dental appliance or dental workpiece from the mold, f) optionally sintering the dental appliance or dental workpiece and to a dental appliance obtainable by such a process.

15 Claims, 3 Drawing Sheets

(56) References Cited

U.S. PATENT DOCUMENTS

| | | |
|---|---|---|
| 4,115,487 A | 9/1978 | Rockett |
| 4,153,403 A | 5/1979 | Schneider |
| 4,155,964 A | 5/1979 | Aronow |
| 4,246,086 A | 1/1981 | Hennicke |
| 4,321,042 A | 3/1982 | Scheicher |
| 4,560,666 A | 12/1985 | Yoshida |
| 4,937,928 A | 7/1990 | Van der Zel |
| 5,000,940 A | 3/1991 | Staples |
| 5,028,362 A | 7/1991 | Janney |
| 5,204,055 A | 4/1993 | Sachs |
| 5,342,201 A | 8/1994 | Oden |
| 5,501,600 A | 3/1996 | Johnson |
| 5,697,043 A | 12/1997 | Baskaran |
| 5,849,068 A | 12/1998 | Hofmann |
| 5,975,905 A | 11/1999 | Kim |
| 5,984,683 A | 11/1999 | Sakata |
| 5,989,031 A | 11/1999 | Kura |
| 6,048,205 A | 4/2000 | Wright |
| 6,059,949 A | 5/2000 | Gal-Or |
| 6,126,732 A | 10/2000 | Hofmann |
| 6,395,202 B1 | 5/2002 | Nagel |
| 6,465,541 B2 | 10/2002 | Bretscher |
| 6,648,645 B1 | 11/2003 | MacDougald |
| 6,740,267 B1 | 5/2004 | Sekino |
| 6,866,929 B2 | 3/2005 | Kodas |
| 6,869,552 B2 | 3/2005 | Glidewell |
| 6,955,776 B1 | 10/2005 | Feenstra |
| 7,086,863 B2 | 8/2006 | Van der Zel |
| 7,181,862 B2 | 2/2007 | Boara |
| 7,236,842 B2 | 6/2007 | Kopelman |
| 7,320,799 B2 | 1/2008 | Zhang |
| 7,384,470 B2 | 6/2008 | Binkle |
| 7,446,057 B2 | 11/2008 | Bietsch |
| 7,536,234 B2 | 5/2009 | Kopelman |
| 7,689,310 B2 | 3/2010 | Kopelman |
| 7,806,694 B2 | 10/2010 | Brodkin |
| 8,721,938 B2 | 5/2014 | Goetzinger |
| 2002/0022677 A1 | 2/2002 | Teramae |
| 2002/0157419 A1 | 10/2002 | Ganguli |
| 2003/0222366 A1 | 12/2003 | Stangel |
| 2004/0026833 A1 | 2/2004 | Culler |
| 2004/0245663 A1 | 12/2004 | MacDougald |
| 2005/0023710 A1 | 2/2005 | Brodkin |
| 2006/0008777 A1 | 1/2006 | Peterson |
| 2006/0257824 A1 | 11/2006 | Pfeiffer |
| 2006/0275738 A1 | 12/2006 | Flanagan |
| 2007/0092853 A1 | 4/2007 | Liu |
| 2008/0131841 A1 | 6/2008 | Taub |
| 2008/0206460 A1 | 8/2008 | Rhoades |
| 2008/0241788 A1 | 10/2008 | Bauer |
| 2008/0302135 A1 | 12/2008 | Costa |
| 2008/0318189 A1 | 12/2008 | Brodkin |
| 2009/0004630 A1 | 1/2009 | van der Zel |
| 2009/0035726 A1 | 2/2009 | Bozdemir |
| 2009/0081616 A1 | 3/2009 | Pfeiffer |
| 2009/0115084 A1 | 5/2009 | Moon |
| 2009/0233258 A1 | 9/2009 | Luthardt |
| 2009/0311650 A1 | 12/2009 | Stephan |
| 2010/0025874 A1 | 2/2010 | Apel |
| 2010/0035215 A1 | 2/2010 | Brodkin |
| 2010/0167238 A1 | 7/2010 | Kopelman |
| 2010/0233655 A1 | 9/2010 | Karim |
| 2010/0248189 A1 | 9/2010 | Burger |
| 2013/0180110 A1 | 7/2013 | Schechner |
| 2013/0209961 A1 | 8/2013 | Rubbert |
| 2013/0295522 A1 | 11/2013 | Chu |

FOREIGN PATENT DOCUMENTS

| | | |
|---|---|---|
| DE | 19922870 | 7/2000 |
| EP | 0311214 | 4/1989 |
| EP | 0455854 | 11/1991 |
| EP | 0943296 | 9/1999 |
| EP | 1250895 | 10/2002 |
| EP | 1258456 | 11/2002 |
| EP | 1252867 | 7/2005 |
| EP | 1561433 | 8/2005 |
| EP | 1661866 | 5/2006 |
| EP | 1972321 | 9/2008 |
| EP | 1992302 | 11/2008 |
| GB | 418160 | 10/1934 |
| JP | 01-258920 | 10/1989 |
| JP | 2004-298599 | 10/2004 |
| WO | WO 94/27517 | 12/1994 |
| WO | WO 97/44291 | 11/1997 |
| WO | WO 01/13814 | 3/2001 |
| WO | WO 01/53225 | 7/2001 |
| WO | WO 03/093195 | 11/2003 |
| WO | WO 2004/063105 | 7/2004 |
| WO | WO 2006/120255 | 11/2006 |
| WO | WO 2007/028787 | 3/2007 |
| WO | WO 2007/051447 | 5/2007 |
| WO | WO 2009/070469 | 6/2009 |
| WO | WO 2010/053698 | 5/2010 |
| WO | WO 2010/074890 | 7/2010 |
| WO | WO 2010/110650 | 9/2010 |
| WO | WO 2010/110662 | 9/2010 |
| WO | WO 2011/041182 | 4/2011 |
| WO | WO 2011/041193 | 4/2011 |
| WO | WO 2011/041194 | 4/2011 |
| WO | WO 2011/075349 | 6/2011 |

OTHER PUBLICATIONS

Patent Search Report; CN Application No. 200980147351.2; Mar. 25, 2013, 2 pgs.

K. Prabhakaran, "Casting of Alumina Using Boehmite as a Binder", Journal Eur. Ceram. Soc., 19 (1999) 2875-2881.

Ullmann's Encyclopedia of Industrial Chemistry (2008), Chapter Silica, Section 4.1 and 5.2.

Ullmann's Encyclopedia of Industrial Chemistry (2005) Chapter Inorganic Polymers, pp. 1-39.

International Search Report PCT/US2009/059154; Jan. 19, 2010; 4 pages.

Beuer et al., "High-Strength CAD/CAM-fabricated veneering material sintered to zirconia coping s—A new fabrication mode for all-ceramic restorations"; Dental Materials 25 (2009) 121-128.

* cited by examiner

PROCESS FOR PRODUCING A DENTAL APPLIANCE

CROSS REFERENCE TO RELATED APPLICATIONS

This is a 35 U.S.C §371 application of PCT/US2009/059154, filed Oct. 1, 2009, which claims priority from EP Application No. 08165607.6, filed Oct. 1, 2008, the disclosures of which are incorporated by reference in its/their entirety herein.

FIELD OF THE INVENTION

In general, the invention relates to a process for producing a dental appliance, comprising steps of providing a mixture of a liquid, an inorganic binder precursor and a glass or glass ceramic powder. The invention also relates to a dental appliance obtainable by such a process as well as the use of a mixture for producing a dental appliance by a casting process.

BACKGROUND ART

Today, dental crowns of glass or glass ceramic materials are typically produced by grinding bodies of compacted and heat treated glass or glass ceramic particles.

The bodies are usually produced by mechanical compacting (e.g. uniaxial pressing) of inorganic powders often together with an organic binder first. The shape of the resulting compacted body is typically limited to the shape of the compacting tool used. Typically, cylindrical or cuboid shaped bodies are obtained.

Hereinafter, the compacted bodies usually undergo a heat treatment to increase the mechanical strength of the compacted bodies. The heat treatment typically takes place at a temperature causing a partially sintering of the powder. During such a sintering step the density of the body of compacted powder is increased to a certain extend.

The thus obtained compacted and heat treated bodies are adhesively fixed in a frame or attached to a holder and are ready for grinding to the desired shape (e.g. a dental crown or dental facing). The grinded bodies are then removed from the frame.

Machining of the compacted bodies which have not been heat treated is typically not possible due to the low mechanical strength of the compacted powder.

In contrast to using a milling process, producing dental appliances using a grinding process would be more desirable, since the wear of the machining tools is reduced and often the final dental work pieces can be produced at a higher speed. Due to the high strength of glass bodies or glass ceramic bodies, milling tools typically cannot be applied successfully and in a commercially meaningful manner.

U.S. Pat. No. 6,648,645 describes a process for fabricating a dental material comprising the steps of mixing ceramic powder and one or more media together to form a putty, applying the putty to a model to conform to the shape of the model and to form a ceramic core material and sintering the model with the putty thereon for a time of less than about 3 hours to provide a dental ceramic core material.

In view of the drawbacks described above, it would be desirable to simplify the process.

DESCRIPTION OF THE INVENTION

The present invention is providing a method for producing a dental appliance which can be used in a milling process, the process typically comprising a reduced number of process steps, e.g. no need for applying mechanical compacting technologies and/or pre-sintering the raw material.

This can be achieved by a process for production of glass or glass ceramic bodies using a casting process, especially a gel casting process.

Thus, in one embodiment the present invention features a process for producing a dental appliance, the process comprising the steps of a) providing a mixture comprising a liquid, an inorganic binder precursor and a glass or glass ceramic powder, and optionally additives including colourants, b) casting the mixture in a mould, optionally into a frame or holder c) drying the cast mixture in the mould to obtain a preferably machinable dental appliance, d) optionally removing the dental appliance from the mould, and e) optionally machining the dental appliance to obtain a dental workpiece, f) optionally sintering the dental appliance or dental workpiece.

The process does not include a pre-sintering step between steps c) and d).

The invention is also directed to a dental appliance obtainable by a process as described in the text of the invention.

In another embodiment, the invention relates to the use of a mixture comprising a solvent, an inorganic binder precursor and a glass or glass ceramic powder for producing a dental appliance by a casting process, the process comprising the steps a) providing a mixture comprising a liquid, an inorganic binder precursor and a glass or glass ceramic powder, b) casting the mixture in a mould.

Yet, the invention is also related to a kit of parts comprising an inorganic binder precursor, a glass or glass ceramic powder and an instruction for use, the kit of parts being to be used in a casting process for producing a dental appliance, wherein the inorganic binder precursor and glass or glass ceramic powder are to be mixed with a liquid.

Moreover, the invention is directed to the use of a dental appliance as described in the text of the invention for producing a dental restoration.

Within the description of the invention, the following terms are defined as follows:

The term "dental article" is to be understood as an article which can and is to be used in the dental or orthodontic area including dental laboratories.

A "dental appliance" means any dental or orthodontic appliance, restoration, dental mill blank or prosthetic device. The appliance may be a finished appliance ready for introduction into the mouth of a patient, or it may be a preformed or near-final dental or orthodontic article subject to further processing before use, such as a dental mill blank.

By "dental mill blank" is meant a solid block of material from which a dental or orthodontic article, dental workpiece or dental restoration can be machined. A dental mill blank may have a size of about 20 mm to about 30 mm in two dimensions, for example may have a diameter in that range, and may be of a certain length in a third dimension. A blank for making a single crown may have a length of about 15 mm to about 30 mm, and a blank for making bridges may have a length of about 40 mm to about 80 mm. A typical size of a blank as it is used for making a single crown has a diameter of about 24 mm and a length of about 19 mm. Further, a typical size of a blank as it is used for making bridges has a diameter of about 24 mm and a length of about 58 mm.

By "machining" is meant milling, grinding, cutting, carving, or shaping a material by a machine. Milling is usually faster and more cost effective than grinding. A "machinable article" is an article having a 3-dimensional shape and having sufficient strength to be machined in a controlled and target-orientated way. That is, material parts of the machinable article can be removed in order to obtain another 3-dimensional shape, which remains dimensional stable for further machining, if desired.

A "dental workpiece" means a dental article or dental appliance which has been further processed e.g. by machining to obtain an intentionally shaped product. A dental workpiece can be further processed e.g. by sintering or used as such.

The term "dental restoration" means any restoration which can be used in the dental field. In this respect, the dental restoration shall have sufficient strength. Dental restorations are typically comprised of at least two parts: a dental framework and a dental veneer. Examples include crowns, abutments and bridges (including 2, 3, 4, 5, 6, 7 or even 8 parts bridges) and implants.

A dental framework or a dental veneer usually has a 3-dimensional inner and outer surface including convex and concave structures. The outer surface of the dental framework typically corresponds essentially to the inner surface of the dental veneer. The inner surface of the dental framework typically corresponds essentially to outer surface of a prepared tooth stump, whereas the outer surface of the dental veneer typically corresponds essentially to the final dental restoration.

Dental ceramic frameworks are typically made of or comprise oxide ceramic materials including $ZrO_2$ or $Al_2O_3$. Compared to other framework such as pottery or paving stones, the dental framework is small and filigree and of high strength. The thickness of the dental framework can vary from very thin, e.g. at the edges and rims (below about 0.1 mm) to considerably thick, e.g. in the biting area (up to about 7 mm). However, dental frameworks may also be made of or comprise metal or metal alloys.

Dental veneers are also small and filigree objects. The strength of dental veneers, however, is typically less compared to dental frameworks. Dental veneers are typically made of or comprise glass or glass ceramic materials.

"Glass" refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former.

A "glass ceramic" means a material sharing many properties with both glass and more traditional crystalline ceramics. It is formed as a glass, and then made to crystallize partly by heat treatment. Unlike sintered ceramics, glass-ceramics have no pores between crystals. Instead, the space between the crystallites is filled by the glassy matrix. Glass ceramics mainly refer to a mixture of lithium-, silicon-, and aluminium-oxides.

"Ceramic" means an inorganic non-metallic material that is produced by application of heat. Ceramics are usually hard, porous and brittle and, in contrast to glasses or glass ceramics, display an essentially purely crystalline structure.

A dental ceramic article or framework is classified as "presintered" within the meaning of the invention if the dental ceramic framework has been treated with heat (temperature range from about 900 to about 1100° C.) for about 1 to about 3 hours to such an extend that the raw breaking resistance (Weibull strength Sigma 0) of the dental ceramic article or framework is within a range of about 15 to about 55 MPa or about 30 to about 50 MPa (measured according to the "punch on three ball test" (biaxial flexural strength) described in DIN EN ISO 6872, edition March 1999, with the following modifications: diameter of steel ball: 6 mm; diameter of support circle: 14 mm; diameter of flat punch: 3.6 mm; diameter of sample disc: 25 mm, thickness of sample disc: 2 mm; no grinding and polishing of samples.).

A presintered dental ceramic article or framework typically has a porous structure and its density (usually 3.0 g/cm$^3$ for an Yttrium stabilized $ZrO_2$ ceramic) is less compared to a completely sintered dental ceramic framework (usually 6.1 g/cm$^3$ for an Yttrium stabilized $ZrO_2$ ceramic). The diameter of the pores can be in a range of about 50 nm to about 150 nm (corresponding to about 500 to about 1500 Å). A typical pore diameter is about 120 nm.

Presintering of a glass or glass ceramic material is typically effected in a temperature range of about 500 to about 750° C.

The terms "sintering" or "firing" are used interchangeably. A pre-sintered ceramic framework shrinks during a sintering step, that is, if an adequate temperature is applied.

The sintering temperature to be applied depends on the ceramic material chosen. For $ZrO_2$ based ceramics a typical sintering temperature range is about 1200° C. to about 1500° C. $Al_2O_3$ based ceramics are typically sintered in a temperature range of about 1300° C. to about 1700° C. Glass ceramic materials are typically sintered in a range of about 700 to about 1100° C. for about 1 to about 3 hours.

Sintering typically includes the densification of a porous material to a less porous material (or a material having less cells) having a higher density, in some cases sintering may also include changes of the material phase composition (for example, a partial conversion of an amorphous phase toward a crystalline phase). A porous material sometimes refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as "closed-porous" structure. It may also be found that instead of the term "cell" sometimes "pore" is used in this technical field.

The structure of a material as referred to in this specification may be categorized as "open-celled", "closed-celled" and "generally free of cells".

The term "open-celled" relates to an "open porosity" according to the mercury porosimetry as defined in DIN 66133. Typical values are between about 6% and about 35%, of between about 15% and about 35%, or between about 30% and about 35%.

The term "closed-celled" relates to a "closed porosity". Closed cells are those cells which are not accessible from the outside and cannot be infiltrated by gases under ambient conditions.

The unit "cells per mm$^2$" is related to the number of cells present on a cross section of the sample to be analysed. A suitable test method is given in DIN 13925.

The volume of a sample can be determined based on the overall outer dimensions of the sample. The density of the sample can be calculated from the measured sample volume and the sample mass. The total volume of glass ceramic material can be calculated from the mass of the sample and the density of the used material.

The total volume of cells in the sample was assumed to be the remainder of the sample volume (100% minus the total volume of material).

A dental ceramic framework is classified as "absorbent" if the dental ceramic framework is able to absorb a certain amount of a liquid, comparable to a sponge. The amount of liquid which can be absorbed depends e.g. on the chemical nature of the dental ceramic framework, the viscosity of the solvent, the porosity and pore volume of the dental ceramic framework. E.g. a pre-sintered dental ceramic article, that is an article which has not been sintered to full density, is able to absorb a certain amount of liquid. Absorbing of liquids is typically only possible if the article has an open-porous structure.

A "particle" means a substance being a solid having a shape which can be geometrically determined. The shape can be regular or irregular. Particles can typically be analysed with respect to e.g. grain size and grain size distribution.

"Density" means the ration of mass to volume of an object. The unit of density is typically $g/cm^3$. The density of an object can be calculated e.g. by determining its volume (e.g. by calculation or applying the Archimedes principle or method) and measuring its mass.

"Sintering" means making objects from a powder, by heating the material (typically below its melting point-solid state sintering) until its particles adhere to each other.

"Casting" means a manufacturing process by which a liquid material (e.g. solution or dispersion) is poured into a mould, which contains a hollow cavity of the desired shape, and then allowed to solidify.

A "sol/gel reaction" is a wet-chemical technique (sometimes also referred to as "Chemical Solution Deposition") for the fabrication of materials starting either from a chemical solution or colloidal particles (e.g. nanoscale particle) to produce an integrated network (gel). Typical precursors are metal alkoxides and metal chlorides, which undergo hydrolysis and polycondensation reactions to form a colloid, a system composed of solid particles (size ranging from 1 nm to 1 μm) dispersed in a solvent. The sol evolves then towards the formation of an inorganic continuous network containing a liquid phase (gel). Formation of a metal oxide involves connecting the metal centers with oxo (M-O-M) or hydroxo (M-OH-M) bridges, therefore generating metal-oxo or metal-hydroxo polymers in solution. The drying process serves to remove the liquid phase from the gel thus forming a porous material. Afterwards, a thermal treatment (firing) may be performed in order to favor further polycondensation and enhance mechanical properties. From a chemical standpoint of view, sol/gel reactions are well known to a person skilled in the art. Sol/gel reactions with respect to silica are described in more detail e.g. in "Ullmann's Encylopedia of Industrial Chemistry (2008), Chapter Silica, Section 4.1 and 5.2. The formation of silica sols, gels and powders is e.g. shown in FIG. 21 on page 36.

Sols are stable disperse systems in which the dispersion medium (or continuous phase) is a liquid and the disperse (or discontinuous phase) is in the colloidal state. A sol can be transferred to a gel due to coagulation of the discontinuous phase. Silica sol is also known as colloidal silica.

A "liquid" is any solvent or liquid which is able to at least partially disperse or dissolve the inorganic binder precursor at ambient conditions (e.g. 23° C.).

An "inorganic binder precursor" is able to undergo or harden via a sol/gel reaction. That is, the inorganic binder precursor can undergo a hydrolysis and/or a polycondensation reaction, thereby forming a sol or colloid. A colloid can be described as a system comprising particles (e.g. having a size ranging from about 1 nm to about 1 μm) dispersed in a solvent.

In contrast to the term "precursor", the term "inorganic binder" refers to the inorganic network formed by the sol/gel reaction. This network ultimately binds the powder particles of the material.

A "hardenable compound" is any compound which can be cured or solidified e.g. by chemical crosslinking through radiation-induced polymerization, crosslinking by using an initiator or heating.

An "initiator" is a substance being able to start the hardening process of a hardenable compound.

The terms "curing", "hardening" or "condensing" are used interchangeable throughout the text and mean the reaction of components with each other thereby creating a network.

"Ambient conditions" mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar.

A composition or solution is "essentially or substantially free of" a certain component within the meaning of the invention, if the composition or solution does not contain said component as an essential feature. Thus, said component is not wilfully added to the composition or solution either as such or in combination with other components or ingredient of other components. A composition being essentially free of a certain component usually contains the component in an amount of less than about 1 wt.-% or less than about 0.1 wt.-% or less than about 0.01 wt.-% or less than about 0.001 wt.-% with respect to the whole composition. Ideally the composition or solution does not contain the said component at all. However, sometimes the presence of a small amount of the said component is not avoidable e.g. due to impurities being present in the raw materials used.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

DETAILED DESCRIPTION OF THE INVENTION

By providing a mixture comprising a solvent, inorganic binder precursor and glass or glass ceramic powder or particles a sol-gel process can be initiated resulting in a homogeneous distribution of the glass or glass ceramic powder or particles in an inorganic network. This can be proven by determining the density gradient in the blocks obtained (mean value of density measurements done on different samples obtained from one casted block, if cutted into pieces). In contrast to this, blocks produced by uniaxial pressing sometimes are inhomogeneous with regard to density. This may be caused by an inhomogeneous pressure distribution in the pressing matrix.

Furthermore, it was found that the slurry obtained was sufficiently stable (meaning that the particles did not precipitate) before and during a casting process.

Compared to a dental appliance manufactured by a pressing process and having insufficient strength unless it is pre-sintered, the dental appliance obtainable according to the gel casting process of the present invention has sufficient strength and can be machined without pre-sintering the dental appliance beforehand.

Moreover, machining is not limited to grinding only but can also be accomplished by milling as well. As outlined above, the strength of the dental appliance is high enough that the dental appliance can be machined without a sintering step, but low enough that the dental appliance can be shaped by applying the more efficient (e.g. faster and cheaper) milling process.

Furthermore, by using an inorganic binder for creating an inorganic network instead of an organic binder, there are less exhaust gases evaporating from the dental appliance during a later heating or sintering step. Organic binders typically produce gases like carbon and/or nitrogen oxides. Preferred embodiments of inorganic binder precursors according to the present invention, if at all, only produce low boiling solvents like alcohols (e.g. methanol and ethanol) which typically evaporate during the drying step.

In addition and in contrast to pressing techniques which are typically limited to specific shapes (e.g., cube and cylinder), the casting process of the invention facilitates the manufacturing of complex shapes. The shape of the obtained dental appliance is only limited to the shape of the mould used. Thus, objects with convex and/or concave structures can be manufactured. This gives the practitioner more freedom to practice.

Compared to pre-sintered dental appliances, the dental appliances obtained by the process of the present invention have a lower density. The lower density does not only facilitate machining of the dental appliance (e.g. extended service life of machining tools) but also reduces the amount of waste which is produced during the shaping process.

The inventive process also allows for the manufacturing of dental appliances with layered structures. E.g. after a first casting step using a mixture A, a second casting step using a mixture B being different in its composition (e.g. with respect to colour) from mixture A can be applied. These steps can be repeated if desired and further mixtures can be used. Finally, a multi-layered dental appliance or block can be obtained. This might be useful for adjusting the colour or the milling parameters.

Moreover, the invention provides an easy process for providing coloured dental appliances. Colouring additives can be added very early in the process (e.g. when the mixture to be casted is provided) and/or later on in the process (e.g. after the drying step). If the colouring is to be done after the drying step, it is typically done by using a colouring solution containing colouring additives (e.g. metal salts).

Adding colouring additives at an early stage in the process, preferably when providing the mixture to be casted, often results in a homogenous distribution of the colouring additives throughout the dental appliance.

The amount of inorganic binder precursor used allows adjusting or influencing the gel time and block toughness. The amount of powder and water used allows adjusting the density of the dried blocks.

The nature and structure of the liquid to be used in the process described in the present invention is not particularly limited, unless the intended purpose cannot be achieved.

Typically the liquid can be characterized by at least one of the following features:
 boiling point: about 60 to about 120° C.,
 freezing point: about −120 to about 0° C., and/or
 density: about 0.7 to about 1.2 g/cm$^3$.

Specific examples of liquids which can be used include water, alcohols (including methanol, ethanol n- and iso-propanol), ketons (including acetone) and mixtures or combinations thereof.

It can be preferred, if the solvent used has similar properties as the by- or condensation products produced during the hardening process or condensing step of the inorganic binder. For example, if during the hardening step a solvent like methanol is produced, the liquid should be miscible with methanol as it is the case for water and alcohols.

The liquid can be present in an amount ranging from about 15 wt.-% to about 60 wt.-%, or from about 20 wt.-% to about 40 wt.-% or from about 25 wt.-% to about 35 wt.-%, with respect to the whole composition or mixture, respectively.

The liquid can be present in an amount of at least about 15 wt.-% or at least about 20 wt.-% or at least about 25 wt.-% with respect to the whole composition or mixture, respectively.

The liquid can be present in an amount up to about 35 wt.-% or up to about 40 wt.-% or up to about 60 wt.-% with respect to the whole composition or mixture, respectively.

The nature and structure of the inorganic binder and its precursor to be used in the process described in the present invention is not particularly limited, either, unless the intended purpose cannot be achieved.

The inorganic binder precursor is typically able to form an inorganic network upon initiating a curing or hardening reaction. The curing or hardening reaction can be initiated e.g. by adjusting the pH value, either by adding acidic or basic reagents including those described in more detail below.

Preferably, the network of the inorganic binder has a similar or essentially identical chemical nature or composition as the chemical nature or composition of the glass/glass ceramic powder/particles used.

The inorganic binder precursor is preferably able to undergo or harden via a sol/gel reaction. That is, the inorganic binder precursor can undergo a hydrolysis and polycondensation reaction, thereby forming a colloid. A colloid can be described as a system comprising particles (e.g. having a size ranging from about 1 nm to about 1 μm) dispersed in a solvent.

Typically the inorganic binder precursor is a liquid at ambient conditions (23° C.; 1013 mbar) or applied as an aqueous solution and can be characterized by at least one of the following features:
 density: about 0.7 to about 1.5 g/cm$^3$ or about 0.9 to about 1.4 g/cm$^3$,
 molecular mass: about 100 to about 500 g/mol or about 150 to about 250 g/mol (for molecular precursors),
 containing Si and O, and/or
 producing low boiling by- or condensation products during hardening, if any (e.g. boiling point below about 120° C.).

Specific examples of inorganic binder precursors which can be used include tetra alkyl (e.g. C1 to C4) orthosilicates (including tetramethyl orthosilicate (TMOS), tetraethyl orthosilicate (TEOS)), water glass and silica sol. That is, the inorganic binder precursor is preferably a material comprising Si—O moieties, but no Si—C moieties.

These binder precursors typically undergo a condensation reaction when the pH value is changed. E.g., orthosilicates typically start condensing at a pH value being in the basic range (e.g. from about 8 to about 14, or from about 10 to about 12), whereas water glass and silica sol start condensing at a pH value being in the acidic range (e.g. from about 0 to about 6 or from about 2 to about 4).

If desired, the progress of the condensation reaction of the inorganic binder system can be monitored using NMR techniques (e.g. $^{29}$Si NMR).

The inorganic binder can be present in an amount ranging from about 0.1 wt.-% to about 40 wt.-%, but preferred from about 1 wt.-% to about 20 wt.-% and most preferred from about 2.5 wt.-% to about 10 wt.-%, with respect to the solids content of the mixture, respectively.

The inorganic binder can be present in an amount of at least about 0.1 wt.-% or at least about 1.0 wt.-% or at least about 2.5 wt.-% with respect to the solids content of the mixture, respectively.

The inorganic binder can be present in an amount up to about 10 wt.-% or up to about 20 wt.-% or up to about 40 wt.-% with respect to the solids content of the mixture, respectively.

The inorganic binder system used does typically not comprise or is essentially free of organic components like polyethylene glycol, polyethylene oxide, polyvinyl alcohols, polyacrylates or silicone polymers.

When using an inorganic binder system as described in the text of the invention, a dental appliance can be obtained which can be machined without conducting a further pre-sintering step. Except of low volatile molecules which might be produced during a condensation reaction, the inorganic binder remains in the dental appliance also during a subsequent machining step.

This is in contrast to binder systems as described e.g. in U.S. Pat. No. 6,648,645 B1 using e.g. polyvinyl alcohols or vinyl terminated polydimethylsiloxanes. These binder systems do not cure by a condensation reaction caused by a change of the pH value. Moreover, these kind of binder systems are typically burned out during a subsequent heating step in order to obtain a pre-sintered material.

The nature and structure of the glass or glass ceramic powder to be used in the process described in the present invention is not particularly limited, either, unless the intended purpose cannot be achieved.

The glass or glass ceramic powder may consist essentially of, or consist only of a glass or glass ceramic material. The glass or glass ceramic material is preferably selected to be compatible for use in human bodies. Furthermore, the glass or glass ceramic material is preferably selected to provide good aesthetic appearance for the dental restoration, in particular when combined with a dental framework.

Typically the glass or glass ceramic powder can be characterized by at least one of the following features:
mean particle size: range from about 5 μm to about 60 μm, or from about 10 to about 40 μm (measured with laser diffraction);
melting temperature: around or less than 1000° C. and/or density: about 2.0 to about 2.6 or about 2.2 to about 2.5 g/cm$^3$ (according to the technical data sheet provided by the manufacturer).

A typical glass composition, which can be used, may include:
silica: about 60 to about 70 wt.-%,
alumina: about 9 to about 13 wt.-%,
potassium-oxide: about 5 to about 10 wt.-%,
sodium-oxide: about 9 to about 13 wt.-%,
lithium-oxide: about 0 to abut 1 wt.-%,
calcium oxide: about 2 to about 5 wt.-%,
barium-oxide: about 0 to about 2 wt.-% (optional),
zirconium oxide: about 0 to about 1 wt.-% (optional), and
cerium-oxide or cerium-fluoride: about 0 to about 1 wt.-% (optional).

Glass or glass ceramic materials which may, for example, be used are generally available under the designations: "VM 9" from Vita Zahnfabrik, Bad Sackingen, Germany, "Cerabien Zr" from Noritake Inc., Japan, "Vintage" from Shofu, Japan; "ZIROX" from Wieland GmbH & Co.KG, Pforzheim, Germany and LM-ZrO$_2$ from Chemichl, Liechtenstein.

The glass or glass ceramic powder can be present in an amount of at least about 40 wt.-% or at least about 60 wt.-% or at least about 65 wt.-% with respect to the whole composition or mixture, respectively.

The glass or glass ceramic powder can be present in an amount up to about 75 wt.-% or up to about 80 wt.-% or up to about 85 wt.-% with respect to the whole composition or mixture, respectively.

The glass or glass ceramic powder can be present in an amount ranging from about 40 wt.-% to about 85 wt.-%, but preferred from about 60 wt.-% to about 80 wt.-% and most preferred from about 65 wt.-% to about 75 wt.-%, with respect to the whole composition or mixture, respectively.

The distribution of the particle size may be for example:
10% of the particles smaller than about 5 μm or smaller than about 2 μm;
50% of the particles smaller than about 25 μm or smaller than about 10 μm; and
90% of the particles smaller than about 70 μm or smaller than about 40 μm.

The mixture might also comprise further components or additives including colorant(s) and/or pigments (e.g. traces of fluorescent, organic pigments e.g. for easier identification of the blocks ("labeling"), which are typically burnt out during firing; inorganic pigments that remain in the appliance for coloration of the sintered material). These additives or components might also be present or included in the glass or glass ceramic powder or particles. Suitable colorants typically comprise one or more of the following elements or ions thereof: Fe, Mn, V, Cr, Zn, Sn and Co.

Further additives, which can be added, include retarders, (such as 1,2-diphenylethylene), plasticizers (including polyethylene glycol derivatives, polypropylene glycols, low-molecular-weight polyesters, dibutyl, dioctyl, dinonyl and diphenyl phthalate, di(isononyl adipate), tricresyl phosphate, paraffin oils, glycerol triacetate, bisphenol A diacetate, ethoxylated bisphenol A diacetate, and silicone oils), and fluoride releasing materials.

There is no need for additives to be present at all, however, if they are present, they can be present in an amount of at least about 0.01 wt.-% or at least about 0.1 wt.-% or at least about 1 wt.-% with respect to the whole composition or mixture, respectively.

Additives can be present in an amount up to about 20 wt.-% or up to about 10 wt.-% or up to about 5 wt.-% with respect to the whole composition or mixture, respectively.

Thus, typical ranges for additives include from about 0.01 to about 20 wt.-% or about 0.1 to about 10 wt.-% or about 1 to about 5 wt.-%.

As long as the additive does not influence the sol gel reaction, it can be employed in any desired amount with respect to the whole composition or mixture.

A mixture to be used for the casting process of the present invention typically comprises the individual components in the following amounts:

Liquid: from about 15 wt.-% to about 60 wt.-% or from about 20 wt.-% to about 40 wt.-% or from about 25 wt.-% to about 35 wt.-% with respect to the whole weight of the mixture.

Inorganic Binder: from about 0.1 wt.-% to about 40 wt.-% or from about 1 wt.-% to about 20 wt.-% or from about 2.5 wt.-% to about 10 wt.-% with respect to the solids content of the mixture.

Glass or glass ceramic Powder: from about 40 wt.-% to about 85 wt.-% or from about 60 wt.-% to about 80 wt.-% or from about 65 wt.-% to about 75 wt.-% with respect to the whole weight of the mixture.

Additives (including colorant(s)): from about 0.01 to about 20 wt.-% or about 0.1 to about 10 wt.-% or about 1 to about 5 wt.-% with respect to the whole weight of the mixture.

The ratio (with respect to weight) of liquid to inorganic binder precursor is typically in a range of about 10:1 to about 1:1 or about 7:1 to about 3:1. If the ratio is outside this range, it might happen that the obtained dental appliance does not show the desired properties.

The ratio (with respect to weight) of inorganic binder to glass or glass ceramic powder can be in a range of about 1:100 to about 1:5 or about 1:40 to about 1:10. If the ratio is outside this range, it might happen that the obtained dental appliance does not show the desired properties.

A possible process of production according to the invention comprises the steps of
a) providing a mixture of a liquid, an inorganic binder precursor and a glass or glass ceramic powder,
b) casting the mixture in a mould,
c) drying the cast mixture in the mould to obtain a dental appliance,
d) optionally removing the dental appliance from the mould, and
e) optionally machining the dental appliance to obtain a dental workpiece,
f) optionally sintering the dental appliance or dental workpiece.

Figure 1A:
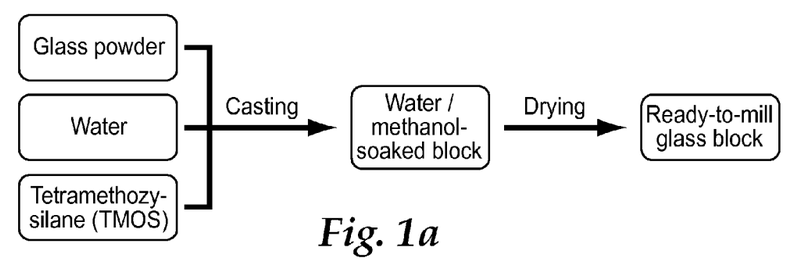
FIG. 1a and FIG. 1b show flow charts of exemplary gel casting processes.

An embodiment of an inventive process is exemplified in FIG. 1a. Glass ceramic powder, tetramethyl orthosilicate (TMOS) and water are combined and cast in a mould to form a cast water and methanol containing block. After drying, a ready-to-mill block is obtained.

The mixture is typically obtainable by a process comprising the steps of:
i) providing a liquid,
ii) adjusting the liquid to a pH value suitable to start the condensation reaction, depending on the binder precursor used (e.g. 10 to about 12 for TMOS or about 2 to about 4 for water glass),
iii) adding the glass or glass ceramic powder and
iv) adding the inorganic binder precursor,
wherein steps iii) and iv) can also be carried out in reverse order.

A further embodiment comprises the steps of:
i a) providing a liquid,
ii a) adjusting the liquid to a pH value suitable to start a condensation reaction of a binder precursor (b),
iii a) adding the glass or glass ceramic powder and
iv a) optionally adding an inorganic binder precursor (a), to obtain slurry I
i b) providing a liquid,
ii b) adding the glass or glass ceramic powder and
iii b) adding the inorganic binder precursor (b), to obtain slurry II
iv) mixing of slurries (I) and (II).

Steps iii a) and iv a) or ii b) and iii b) can also be carried out in reverse order, respectively. (a) and (b) refer to two different binder precursors (e.g. (a)=silica sol and (b)=water glass). In case that only precursor (b) is used in this embodiment, it still differs from the embodiment above in that regard that two homogeneous powder slurries are mixed, which may lead to a better and faster mixing.

Figure 1B:
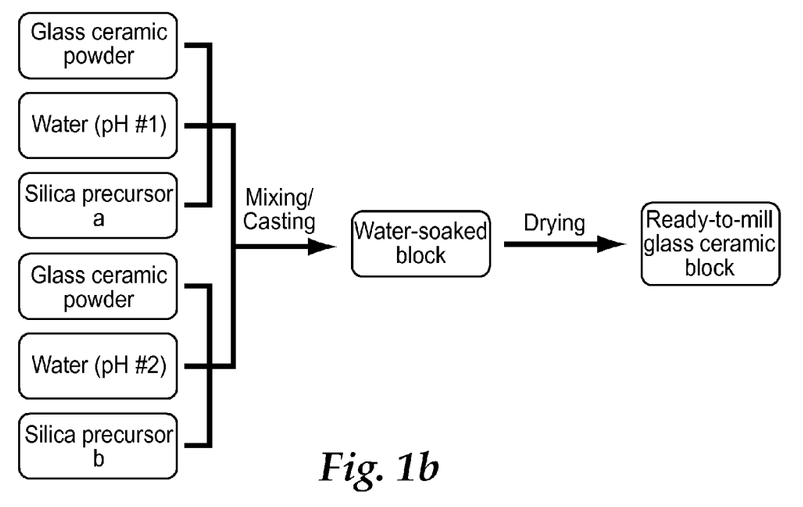

Such a process is exemplified in FIG. 1b. Glass ceramic powder, a silica precursor (a) and water are combined to obtain slurry I. Glass ceramic powder, a silica precursor (b) and water (e.g. having a different pH value than the water of slurry I) are combined to obtain slurry II. Slurry I and slurry II are combined and cast in a mould to obtain a cast water-soaked block. After drying, a ready-to-mill glass ceramic block is obtained.

The embodiment described in FIG. 1b (with precursor (a)=silica sol and (b)=water glass) might be advantageous if homogeneous slurries are desirable, which essentially do not contain any organic substance. In this particular embodiment, all components used are miscible with water.

The pH value can be adjusted by using conventional basic reagents like NaOH, KOH or $NH_3$ containing solutions or acidic reagents like HCl or $HNO_3$ containing solutions, wherein the pH value is typically determined during the adjustment step. The pH value can be determined by e.g. pH sensitive paper or electronic equipment (e.g. pH electrode). If strong acids or bases are employed, determination of the pH value can also be obtained via calculation from the amount of acid used.

The inorganic binder precursor is typically added rapidly while the solution is stirred. The addition of the inorganic binder precursor usually marks the starting point of a sol-gel reaction caused by the reaction of the precursor molecules. If a two-slurry system ("I" and "II") is used, mixing of the two slurries marks the starting point of the sol-gel reaction.

During the sol-gel reaction typically an inorganic network is formed.

The mixture of process step a) can be characterized by at least one of the following features:
time needed for gelation (i.e. time from adding the inorganic binder precursor until solidification of the mixture to the point that it cannot be deformed or removed from the mould by tilting the mould): 30 seconds to 5 minutes and/or
time needed for settling (i.e time from stopping the mixture being stirred until the mixture becomes inhomogeneous because of settling of the glass or glass ceramic particles): 7 minutes to more than one week (values were obtained either without inorganic binder precursor present or with precursor present but at a pH value that inhibits gelation).

The casting step according to process step b) can be characterized by at least one of the following features:
duration: about 2 to about 5 seconds for 10 g of reaction mixture and/or
temperature: about 10 to about 40° C. or about 15 to about 30° C. or at ambient conditions (e.g. 23° C.).

During casting the mixture into a mould the inclusion of air bubbles in the cast mixture should be avoided. For this purpose, application of reduced pressure is recommended.

The mould which is used for receiving the mixture can be characterized by at least one of the following features:
volume of the mould: can be less than about 1 $cm^3$ or can be above about 20 $cm^3$; useful ranges include 0.2 $cm^3$ to about 50 $cm^3$ or about 0.5 $cm^3$ to about 30 $cm^3$,
dimensions of the mould: arbitrary, as long as there are no cavities too small to be filled by the reaction mixture, shape of the mould: arbitrary, as long as there are no cavities too small to be filled by the reaction mixture and/or
material of the mould: silicone, polyethylene (PE), polypropylene (PP), polycarbonate, polyurethane, polystyrene, metal (e.g. steel), etc.

Thus, the mould can have a regular (e.g. cubic like or cylindric like) or irregular shape (e.g. shape of a tooth, veneer, inlay, onlay, crown, bridge, orthodontic bracket). By shape of the mould, the shape of the positive model is meant, obtained after de-moulding the cast and dried mixture from the mould.

According to a particular embodiment, the mould has the shape of a dental veneer to be manufactured, typically slightly oversized (e.g. up to about 20 vol.-% or up to about 10 vol.-%) compared to the final size of the veneer (i.e. the shape of veneer in the patients mouth). Examples of shapes of dental veneers are given e.g. in WO 2007/028787 or U.S. Pat. No. 5,342,201, the description of which with respect to the shape of veneers is regarded as part of this description and is herewith incorporated by reference.

In the mould there might also be embedded a holder. Thus, the dental appliance after having been removed from the mould may contain a holder or may be fixed to a holder. This allows a more convenient handling of the dental appliance in a further processing or machining step. The holder is typically formed of metal. The holder may have the shape of a post. According to a preferred embodiment, the holder may have a shape allowing the holder to be placed in and/or supported by a working machine. An example of a suitable holder is shown in EP 0 455 854 B1, especially FIG. 2.

The drying step can be characterized by at least one of the following features:
 duration: up to about 24 h or up to about 8 h or up to about 3 h,
 temperature: from about 10 to about 120° C. or about 20 to about 100° C., and/or
 pressure: ambient pressure.

During the drying step, the network-formation is typically finalized and low boiling components which may have been generated during the network forming process, if any, can evaporate from the cast mixture.

Drying can be performed at ambient conditions by simply letting the mould containing the mixture stand for a sufficient period of time. If a more rapid drying is desired, this step is typically performed in a drying oven.

A machining step is optional. If it is carried out, it can be characterized by at least one of the following features:
 machining can be accomplished by either grinding or milling or a combination of both,
 machining can be accomplished under dry or wet conditions,
 milling parameter rotation: about 18,000 to about 32,000 rpm (rotations per minute), and/or
 milling parameter motion: about 1,500 to about 2,500 mm per minute.

Other machining equipment as those mentioned in the description of the invention can be used, if desired.

A sintering step is optional, too. If it is carried out, it can be characterized by at least one of the following features:
 duration: about 10 to about 60 min or about 20 to about 25 min,
 temperature: about 600 to about 900° C. or about 750 to about 850° C.,
 pressure: about 10 to about 50 mbar or about 15 to about 35 mbar, and/or
 atmosphere: air.

Sintering can be conducted in a commercially available sinter furnace (e.g. Austromat 3001 from Dekema Comp.; Germany).

Sintering, if at all, can be conducted before the dental workpiece is machined or afterwards.

Moreover, sintering, if at all, can be conducted before the dental workpiece or dental appliance is placed on a dental framework.

If the dental workpiece has the shape of a dental veneer it can be preferred, if the sintering step is conducted after the dental workpiece has been placed on a dental framework.

It has been found that the sintering behaviour of the inventive dental appliances analysed by dilatometry is very homogeneous. There is especially advantageous behaviour at temperatures up to 500° C., where the inventive material displays only little dimensional change due to the overlap of thermal expansion and sintering shrinkage (see FIGS. 3*a* and 3*b*).

The breaking resistance of the sintered material obtainable after a sintering step is typically in a range of about 50 to about 400 MPa, or in a range of about 50 to about 120 MPa measured according to the "punch on three ball test" as specified in ISO 6872.

The sintered material typically has a density in a range of about 2 g/cm$^3$ to about 2.7 g/cm$^3$.

The sintered material typically shows a certain translucency. The translucency is usually specified by the opacity of a material relative to daylight. Typical ranges of the opacity of the sintered material are about 50% to about 60% (typically corresponding to natural dental enamel), about 60% to about 80% (typically corresponding to natural dentine) and about 80% to about 90% (typically corresponding to natural opaque dentine).

The invention is also directed to a dental appliance obtainable by a process as described in the text of the invention (that is, the product obtainable after a drying step, but before an optional sintering step).

The dental appliance can be characterized by at least one of the following features:
 raw breaking resistance: about 1 to about 10 MPa or about 2 to about 5 MPa (measured according to "punch on three ball test" as specified in ISO 6872);
 density: about 1.2 to about 1.7 g/cm$^3$ (based on determination of volume and mass; 23° C.) and/or
 pore volume: about 25 to about 65% (derived from density measurements).

The dental appliance may be substantially free of cells, however may comprise up to about 20 cells per mm$^2$. Preferably, the dental appliance may comprise about 4 to about 10 cells per mm$^2$. The cells may have a diameter of less that about 150 µm, or less than about 100 µm or less than about 50 µm.

The volume of the cells in the dental appliance relative to the total volume of the dental appliance as referred to in this specification is typically in a range of about 20% to about 40%, and more preferably in a range of about 30% to about 38%.

Figure 2A:
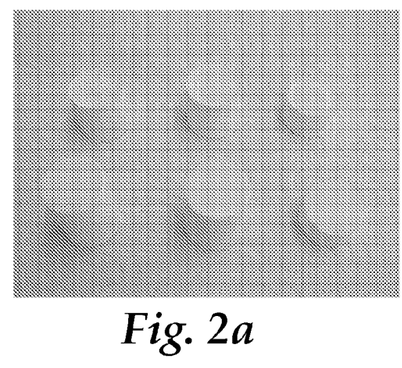
FIG. 2a shows a sample of a block after removal from the mould.
Figure 2B:
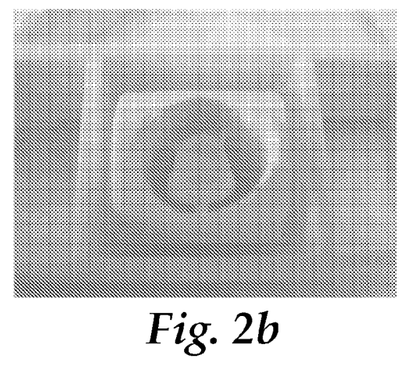
FIG. 2b shows a milled incisor cap obtained from a casted and dried block.

Examples of dental appliances obtainable according to the inventive process are shown in FIGS. 2*a* and 2*b*. FIG. 2*a* shows cylindrical blocks after removal from the mould. FIG. 2*b* shows a dental workpiece obtained after machining the dental appliance. The dental workpiece of FIG. 2*b* has the shape of a dental veneer for a dental crown.

In another embodiment of the invention, the surface of the dental workpiece, especially after a sintering step, may be glazed. This may be advantageous to achieve a good optical appearance of the final dental restoration and/or to render the dental restoration more durable. The glazing is typically done with a composition having a color within the range of colors of human teeth. Further, the glazing preferably has a translucency similar of human teeth. The glazing may comprise materials having different colors and a certain degree or certain degrees of translucency, for example, to provide an optical appearance resembling that of natural teeth.

The invention is also directed to a kit of parts comprising the parts inorganic binder precursor, glass or glass ceramic powder and instruction for use, the kit of parts to be used in a casting process for producing a dental appliance, wherein the inorganic binder precursor and glass or glass ceramic powder are to be mixed with a solvent/liquid.

The kit of parts may further comprise one or more moulds or raw material from that a mould can be shaped (e.g. wax).

The mixture to be used in the process of the present invention does typically not contain polymerizable organic binder components like (meth)acrylate or epoxy groups containing components.

Thus, according to one embodiment of the invention the mixture is essentially free of polymerizable organic binder components. An organic binder within the meaning of the invention is a binder, which consists of organic compounds that are added to strengthen the appliance or workpiece and cannot be thermally removed from the workpiece below a temperature of 200° C. Organic binders typically produce gases like carbon oxide(s) or nitrogen oxide(s) when heated above the combustion temperature. These exhaust gases have to be removed by expensive air treatment or chimneys.

Moreover, the addition or presence of an initiator (e.g. photo or redox initiator) for starting the hardening process of the inorganic binder precursor is typically not needed. The hardening process can be initiated by adjusting the pH value or simply by employing a diluted acidic/basic solution.

The production process of the present invention does typically also not comprise a pressing step (e.g. isostatic or uniaxial) or a pre-sintering step.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope thereof.

The following examples are given to illustrate, but not limit, the scope of this invention.

EXAMPLES

Unless otherwise indicated, all parts and percentages are on a weight basis, all water is deionized water, and all molecular weights are weight average molecular weight. Moreover, unless otherwise indicated all experiments were conducted at ambient conditions (23° C.; 1013 mbar).

Measurements

Density

Density measurements of as synthesized and sintered materials were performed by determination of the volume of symmetric blocks and their mass.

Toughness of Sintered Bodies

Toughness or bending strength was determined using a commercially available device (INSTRON 5566; Zwick Comp.) according to the instruction of use provided by the manufacturer.

Particle Size

The mean particle size was determined using a commercially available granulometer (Laser Diffraction Particle Size Analysis Instrument, CILAS 1064; CILAS Comp.) according to the instruction of use provided by the manufacturer.

Homogeneity

Homogeneity of the prepared bodies was determined by measuring the density of different blocks within one batch and the density of different sections within one block.

pH Value

The pH-value was determined using a mobile pH-indicator paper available from Merck KGaA, Darmstadt Germany (pH 0-14, pH indicator strips, non bleeding, Art. No. 1.09535.0001). Additionally, pH measurements were performed employing a pH electrode and measurement device "744 pH meter" from Metrohm.

Dilatometry

Dilatometry curves for analysis of shrinkage during sintering were obtained employing a commercially available dilatometer (Baehr DIL 802) according to the instruction of use provided by the manufacturer.

Abbreviations

Table 1 describe some of the components used in the Examples below in more detail.

TABLE 1

| Name | Description |
|---|---|
| TMOS | Tetramethyl orthosilicate |
| LM-ZrO$_2$ | 97-100% SiO$_2$, Al$_2$O$_3$, K$_2$O, Na$_2$O, CaO, La$_2$O$_3$, ZnO$_2$, B$_2$O$_3$, CeO$_2$, SrO, SnO$_2$, Li$_2$O, F, P$_2$O$_5$, 0-3% shading components |
| GM32087 | 50% SiO$_2$, 1% BaO, 20% SrO, 15% B$_2$O$_3$, 15% Al$_2$O$_3$ |

Example 1

7.6 ml of de-ionized water were adjusted to a pH value of 11 using sodium hydroxide (0.25 M). To this solution, 6.4 ml of tetramethyl orthosilicate (TMOS) were added and vigorously stirred. The addition of TMOS marks the starting point of the sol-gel reaction. Immediately after this, 24.8 g of glass powder (LM-ZrO2) were dispersed into the solution, while the slurry was still being stirred. The glass powder used was ball milled to a mean particle size of about 17 μm. About 50 s after addition of the powder, the slurry was cast into cylindric silicone moulds (Dreve Dublisil-30). Gelation was complete after about 60 to about 90 s. Afterwards, the blocks were dried inside the moulds under ambient conditions over 24 h. The dried blocks could easily be removed from the moulds. The obtained blocks had a density of about 1.4 g/cm$^3$ and displayed toughness sufficient for handling and milling.

Example 2

The procedure was carried out as in Example 1, but using 8.8 ml of de-ionized water, 3.2 ml of TMOS and 24.8 g of glass powder. The slurry was cast into the moulds after 30 s reaction time. Gelation was complete after about 60 to about 90 s. The blocks produced had a density of about 1.30 g/cm$^3$.

Example 3

The procedure was carried out as in Example 1, except that the glass powder was added to the water first and then vigorously stirred. After that, TMOS was added. 8.4 ml of de-ionized water, 25.0 g of glass ceramic powder and 1.6 ml of TMOS were used. The slurry was cast into the moulds after about 60 seconds of reaction time, gelation was complete after about 300 seconds. The blocks produced had a density of 1.38 g/cm$^3$.

Example 4

Two slurries were produced. The first slurry contained 6.7 ml de-ionized water, 2.0 ml silica sol (LEVASIL™ 200/40%), 0.15 ml of hydrochloric acid (30%; Fluke) and 25.0 g of glass ceramic powder (PFM-98N) having a mean particle size of about 6 μm. The second slurry contained 4.3 ml deionized water, 0.1 ml water glass (Aldrich) and 12.5 g of glass ceramic powder (PFM-98N) having a mean particle size of about 6 μm. The two slurries were cast at a volume ratio of 2:1 directly into PE moulds via a static mixing unit. Gelation was complete after several minutes. Drying procedures can be executed as in Example 1. The obtained blocks had a density of about 1.60 g/cm$^3$ and a toughness of 1.8 MPa.

| Example | Density [g/cm$^3$] | Density variation within one block* [g/cm$^3$] | Toughness [MPa] | Porosity** [%] |
|---|---|---|---|---|
| 1 | 1.40 | n.a. | n.a. | 42 |
| 2 | 1.30 | n.a. | n.a. | 46 |
| 3 | 1.38 | block density +/− 0.01 | n.a. | 43 |
| 4 | 1.60 | block density +/− 0.02 | 1.8 | 33 |

*Mean value of density determination (mass/volume) done on 5 samples obtained when cutting a block into 5 pieces.
**Porosity has been calculated based on the dimension and the mass of the analysed blocks taking into account the density of the sintered material (containing no pores).

For milling tests, the dried blocks were glued into plastic frames from 3M ESPE. Incisor caps were milled from these blocks using a LAVA Form milling machine.

The blocks obtained after drying were cut into discs of 2 mm thickness and into sticks with the dimensions 4 mm×4 mm×20 mm. The sticks were used for dilatometry (employing a Baehr DIL 802). The discs were sintered at 810° C. and 25 mbar pressure to obtain dense glass material that was checked for its optical properties.

Figure 3A:
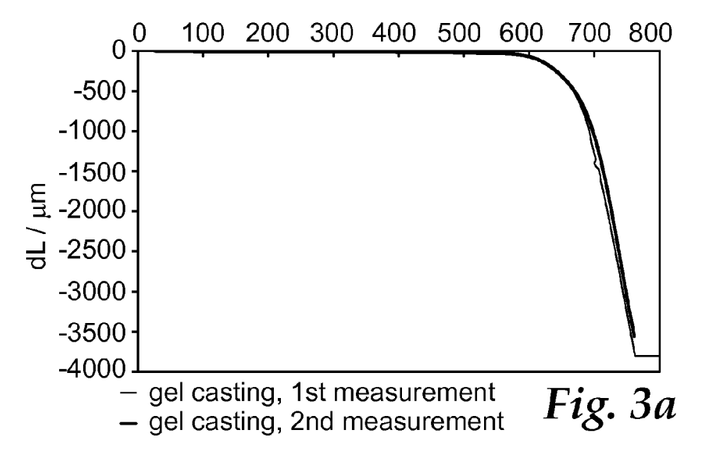
FIG. 3a and FIG. 3b show dilatometry curves of material obtained by gel casting.
Figure 3B:
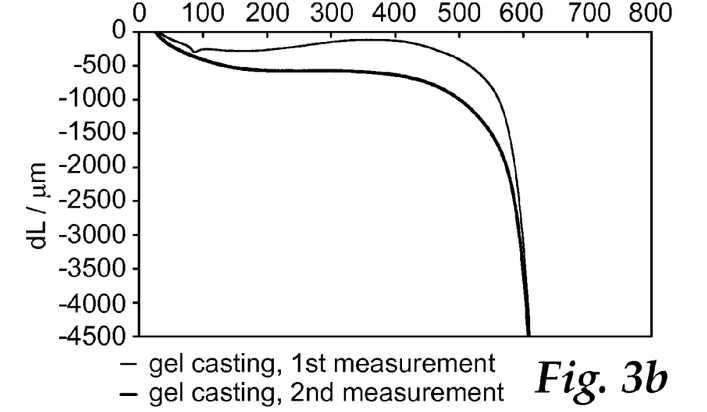

In FIGS. 3a and 3b dilatometry curves of samples obtained by the gel casting route is shown. FIG. 3a: entire dilatometry curve; FIG. 3b: magnification of the range before major shrinkage occurs. The blocks analysed showed a homogeneous sintering and shrinking behaviour.

Figure 4:
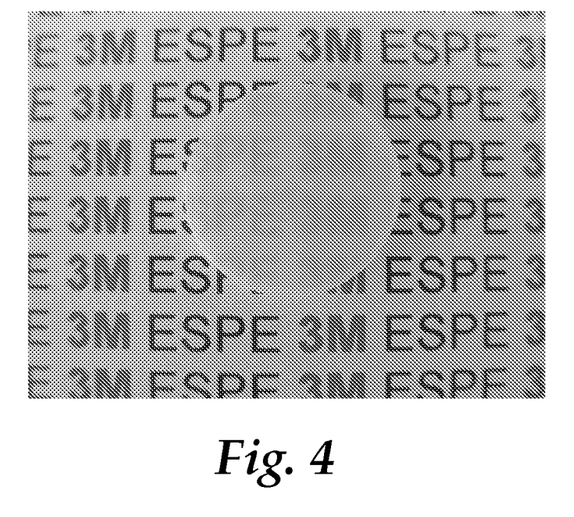
FIG. 4 shows a sintered disc prepared by gel casting.

FIG. 4 shows a sample of a sintered disc of material obtained via the gel casting route. Transparency is satisfactory regarding aesthetic requirements of dental restorations.

The invention claimed is:

1. A process for producing a dental appliance, the process comprising the steps of
   a) providing a mixture of a liquid, an inorganic binder precursor containing Si and O and a glass or glass ceramic powder, wherein the glass or glass ceramic powder is present in the mixture in an amount of about 60 wt.-% to about 85 wt.-%,
   b) casting the mixture into a mould,
   c) drying the cast mixture in the mould to obtain a machinable dental appliance,
   the inorganic binder precursor being able to undergo a sol/gel reaction, the mixture being obtained either by a process comprising the steps of:
      i) providing the liquid,
      ii) adjusting the liquid to a pH value suitable to start a condensation reaction, depending on the inorganic binder precursor used,
      iii) adding the inorganic binder precursor,
      iv) adding the glass or glass ceramic powder,
   wherein steps iii) and iv) can also be carried out in reverse order;
   or by a process comprising the steps of:
      i a) providing the liquid,
      ii a) adjusting the liquid to a pH value suitable to start the condensation reaction of a binder precursor (b), to be added later,
      iii a) adding a glass or glass ceramic powder and
      iv a) optionally adding an inorganic binder precursor (a), to obtain slurry I,
      i b) providing a liquid,
      ii b) adding a glass or glass ceramic powder and
      iii b) adding an inorganic binder precursor (b), to obtain slurry II
      iv) mixing of slurries I and II,
   wherein steps iii a) and iv a) or ii b) and iii b) can also be carried out in reverse order.

2. The process according to claim 1, the inorganic binder precursor being selected from orthosilicates, silica sol, water glass, mixtures and combinations thereof.

3. The process according to claim 1, the mixture being characterized by the pH-value (aqueous composition) being in the basic range if the inorganic binder precursor comprises a tetra alkyl orthosilicate.

4. The process according to claim 1, the casting step being characterized by at least one of the following features:
   duration: about 1 to about 10 s for 10 g of mixture, and/or
   temperature: about 10 to about 40° C.

5. The process according to claim 1, the mould being characterized by at least one of the following features:
   volume of mould: from about 0.5 cm$^3$ to about 100 cm$^3$,
   shape: designed to obtain cubic, cylindric, tooth, veneer, bridge, crown, inlay, onlay, orthodontic bracket like structure, and/or
   material of mould: silicone, polyethylene, polypropylene, polycarbonate, polyurethane, polystyrene or metal.

6. The process according to claim 1, the drying step being characterized by at least one of the following features:
   duration: up to about 24 h,
   temperature: from about 10 to about 120° C., and/or
   pressure: ambient pressure.

7. The process according to claim 1, the liquid being characterized by at least one of the following features:
   boiling point: about 60 to about 120° C.,
   freezing point: about −120 to 0° C., and/or
   density: about 0.7 to about 1.2 g/cm$^3$.

8. The process according to claim 1, the inorganic binder precursor being characterized by at least one of the following features:
   liquid at ambient conditions (23° C.) or applicable as aqueous solution or dispersion,
   density: about 0.7 to about 1.5 g/cm$^3$,
   molecular mass: about 100 to about 500 g/mol, and/or
   producing only low boiling by- or condensation products during hardening.

9. The process according to claim 1, the glass or glass ceramic powder being characterized by at least one of the following features:
   mean particle size: range from about 5 μm to about 60 μm, (measured with laser diffraction; 23° C.),
   melting temperature: below about 1000° C., and/or
   density: about 2.0 to about 2.6 g/cm$^3$.

10. The process according to claim 1, further comprising repeating steps a)-c) and optionally steps d)-f) of claim 1 at least twice to obtain a dental appliance with a layered structure.

11. The process according to claim 1, the mixture being characterized by the pH-value (aqueous composition) being in the acidic range if the inorganic binder precursor comprises water glass, silica sol, mixtures or combinations thereof.

12. The process according to claim 1, further comprising machining the dental appliance.

13. The process according to claim 12, wherein machining the dental appliance includes machining the dental appliance prior to sintering the dental appliance.

14. The process according to claim 1, further comprising removing the dental appliance from the mould.

15. The process according to claim 1, wherein the mixture is essentially free of polymerizable organic binder components.

\* \* \* \* \*

UNITED STATES PATENT AND TRADEMARK OFFICE
CERTIFICATE OF CORRECTION

PATENT NO. : 8,865,033 B2
APPLICATION NO. : 13/060127
DATED : October 21, 2014
INVENTOR(S) : Gallus Schechner It is certified that error appears in the above-identified patent and that said Letters Patent is hereby corrected as shown below:

Title Page: Item 57 (Abstract)
Line 5, Delete "mold," and insert -- mould, --, therefor.
Line 6, Delete "mold" and insert -- mould --, therefor.
Line 9, Delete "mold," and insert -- mould, --, therefor.

In the Specification

Column 5
Line 48, Delete "Encylopedia" and insert -- Encyclopedia --, therefor.

Column 8
Line 11, Delete "ketons" and insert -- ketones --, therefor.

Column 16
Line 46, Delete "(LM-ZrO2)" and insert -- (LM-ZrO$_2$) --, therefor.

Signed and Sealed this
Twenty-first Day of April, 2015

Michelle K. Lee
*Director of the United States Patent and Trademark Office*